United States Patent [19]

Brooks

[11] 4,151,086
[45] Apr. 24, 1979

[54] FLUID SAMPLE COLLECTION AND DISTRIBUTION SYSTEM

[76] Inventors: Robert A. Frosch, Administrator of the National Aeronautics and Space Administration, with respect to an invention of Richard L. Brooks, Conroe, Tex.

[21] Appl. No.: 893,382

[22] Filed: Apr. 4, 1978

[51] Int. Cl.² ............................................. B01D 23/24
[52] U.S. Cl. .................................... 210/108; 210/142; 73/714
[58] Field of Search .................. 210/82, 90, 102, 108, 210/141, 142; 73/714, 717

[56] References Cited

U.S. PATENT DOCUMENTS

| | | | |
|---|---|---|---|
| 1,520,668 | 12/1924 | Wilkin | 210/90 X |
| 2,828,017 | 3/1958 | Ronningen et al. | 210/102 |
| 3,441,136 | 4/1969 | Serfass et al. | 210/90 |
| 4,060,485 | 11/1977 | Eaton | 210/90 X |

Primary Examiner—William A. Cuchlinski, Jr.
Attorney, Agent, or Firm—Marvin J. Marnock; John R. Manning; Marvin F. Matthews

[57] ABSTRACT

A multi-point fluid sample collection and distribution system is provided wherein the sample inputs are made through one or more of a plurality of sampling valves to a progressive cavity pump which is not susceptible to damage by large unfiltered particles. The pump output is through a filter unit that can provide a filtered multi-point sample. An unfiltered multi-point sample is also provided. An effluent sample can be taken and applied to a second progressive cavity pump for pumping to a filter unit that can provide one or more filtered effluent samples. The second pump can also provide an unfiltered effluent sample. Means are provided to periodically back flush each filter unit without shutting off the whole system.

18 Claims, 2 Drawing Figures

FLUID SAMPLE COLLECTION AND DISTRIBUTION SYSTEM

ORIGIN OF THE INVENTION

The invention described herein was made in the performance of work under a NASA contract and is subject to the provisions of Section 305 of the National Aeronautics Space Act of 1958, public law 85-568 (72 Stat. 435; 42 U.S.C. 2457).

BACKGROUND OF THE INVENTION

1. Field of the Invention

The present invention generally relates to methods and apparatus for collecting an aqueous sample for use in making a qualitative analysis of the sample to determine the condition thereof. More particularly, the invention relates to methods and apparatus for automatically and continuously collecting samples from any one of a plurality of sampling points, filtering part of the samples collected and delivering both unfiltered and filtered samples to various analyzing sensors for making a determination of the quality of the aqueous supply from which the sample is taken through various electrical, chemical and biological means.

2. Description of the Prior Art

With the increased concern for environmental pollution, methods and apparatus for the qualitative and quantitative analysis of aqueous samples are continually being devised. As these improved methods and apparatus are evolved, the time required to perform the tests necessary has been reduced to the point where the apparatus has been taken out of the laboratory category and is now an on-line process system. However, advances in methods of obtaining samples for analysis, and in particular from a water treatment process plan, have not kept pace with the advances in analysis equipment. Additionally, improvements in the analysis equipment hs levied new requirements for filtration of the samples obtained. Again, performance of prior art filter systems have not kept pace with the new requirements.

In the prior art, systems for collecting fluid samples have for the most part been directed to apparatus which is periodically energized to draw the fluid through a sample chamber and into a collection container. With the older, laboratory-type method of testing, which did not require a high volume of waste water effluent to be collected in a short time interval, these methods were adequate. For example, see Peterson, U.S. Pat. No. 3,986,401, which shows a composite sampling method and system for collecting fluid samples from a high velocity effluent. As above-mentioned, the system comprises a pump which is periodically energized to draw fluids through a sample chamber and into a collection container, which may be connected into a testing apparatus or, more conventionally, with the container being periodically transported to a laboratory for subsequent testing of the contained sample.

Prior art filter systems, particularly those associated with silt laden or wastewater discharge, frequently clog with filtrate, requiring cleaning to unclog the filters. In the past, such cleaning has been provided through a backwash or through a flushing process, sometimes known as a "blow-down", involving a rapid rush of unfiltered liquid over but not through the filter mesh element, forcing the clogging material off the filter to a discharge opening for removal. Both of the above-described methods are particularly adaptable for use with the above-described collection system whereby samples are obtained from a process stream only periodically. However, for a sample collection apparatus designed to provide a continuous flow of filtered and unfiltered sample to be used with modern, quick assay apparatus, it becomes cumbersome and inefficient to periodically interrupt the flow of sample collected in order to clear a clogged filter.

The present invention overcomes the deficiencies in the prior art by providing methods and apparatus for automatically and rapidly providing a continuous flow of sample collected from a plurality of distinct "user" selectable sample points and for providing a plurality of continuous output flows in various stages of filtration whereby interruption of one flow to clear a clogged filter may be programmed around the testing procedure.

SUMMARY OF THE INVENTION

The present invention provides a method and apparatus for automatically collecting fluid samples from any one of a plurality of sampling points along a process flow path for delivering a continuous stream of sample to various chemical and biological analytical sensors whereby a determination of the effectiveness of the process treatment may be ascertained. Although some of the sensors require unfiltered water, other sensors which monitor soluble constituents and biological matter utilize water that is filtered to remove particulate matter as small as 0.45 microns.

In one embodiment of the present invention, an aqueous sample is obtained from various locations in a water treatment system by any one of a plurality of sampling valves, each having the ability to pass large particles without becoming clogged. The valves are connected to a pair of progressive cavity pumps which are not susceptible to damage by large particles as would be present in unfiltered sewage. Two pumps are used in the system, with one associated with a plurality of multi-point sample valves and the remaining pump associated with an effluent sample valve. The system is designed with the capability that the multi-point pump can be switched to pump effluent from an interim line, thereby bypassing the effluent pump. Further, the system also has the capability to use effluent to backflush each of the multi-point lines for either priming each multipoint line or for cleaning the line of debris. Each pump additionally has a by-pass loop which enables an operator to manually adjust the amount of new sample being pumped to the filters. A filter with modified backflush system is associated with each pump and includes four timed control solenoid-operated valves, with two valves associated with each filter system to increase the system output. One filter unit is attached to the multi-point pump with both sides of the filter containing a ten-micronsize, stainless-steel, woven filter. The second filter unit is attached to the effluent pump, and contains two different size filters, one filter is a ten-micron filter and one a 0.45-micron filter. Accordingly, it may be seen that there are five different samples that may be obtained from the pumps and filter units. One is an unfiltered multi-point sample which is pumped directly from the multi-point sample valves. The second is a ten-micron filtered multi-point sample obtained from the multi-point pump filter unit. The third is an unfiltered plant effluent sample obtained from the effluent pump and the fourth and fifth being ten-micron filtered plant effluent and 0.45-micron filtered plant effluent samples obtained from the effluent pump filter assemblies. The system is designed continuously to pump through five different sample lines for use by various sensor analyzers, with unused sample being discharged into a drain for reintroduction back into the process stream. Additionally, the modified backwash system connected with each filter unit may be operated so that only one sample line is shut down at a given period to backwash the filter and therefore clean it. As a result, the backwash of each filter may be sequenced to take advantage of the sensor procedures, thereby minimizing the effect of down time of a particular sample line.

Accordingly, it is a feature of the present invention to provide an automated method and apparatus for obtaining aqueous samples from a plurality of distinct and selectable sample points and continuously present the obtained samples in various stages of filtration to various analyzing sensors.

Another feature of the invention is to provide automated method and apparatus which may be sequenced around the performance of sensor analyzers to permit backwash and cleaning of sample flow filters without interrupting the analyzing sequence.

These and other features and advantages of the present invention will become apparent from the following detailed description when considered in conjunction with the accompanying drawings.

BRIEF DESCRIPTION OF THE DRAWINGS

In order that the manner in which the above-recited advantages and features of the invention are attained can be understood in detail, a more particular description of the invention may be had by reference to specific embodiments thereof which are illustrated in the appended drawings, which drawings form a part of this specification. It is to be noted, however, that the appended drawings illustrate only typical embodiments of the invention and therefore are not to be considered limiting of its scope when the invention may admit to further equally effective embodiments.

In the drawings.

DETAILED DESCRIPTION OF THE PREFERRED EMBODIMENT

Figure 1:
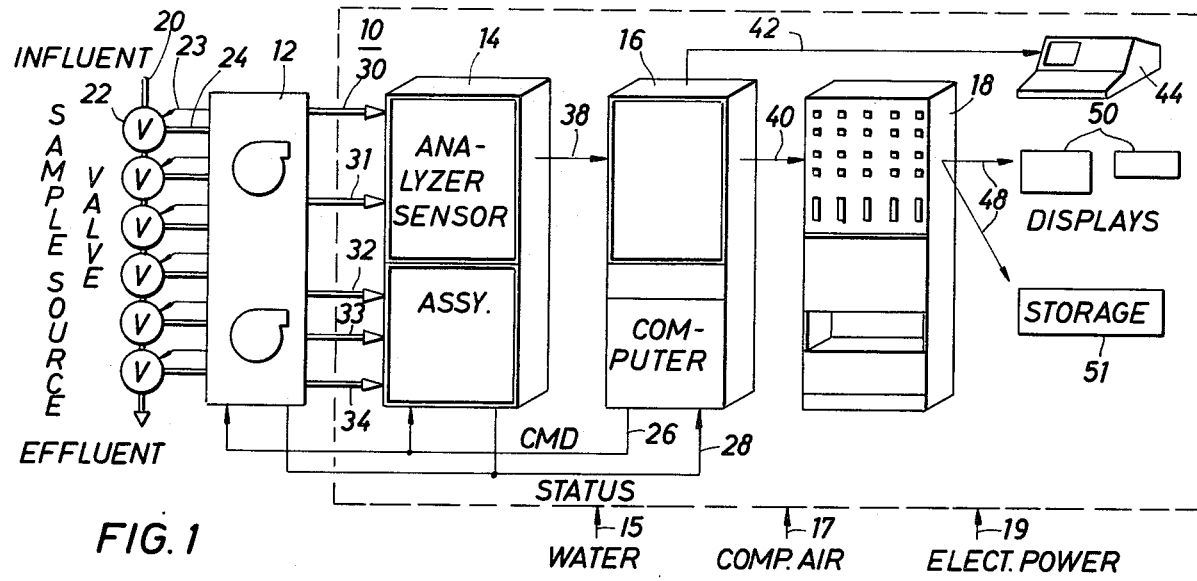
FIG. 1 is a pictorial/block diagrammatic representation disclosing the various assemblies making up a portable water monitoring system of which the present invention forms an important sub-assembly.

Referring now to FIG. 1, an automated water monitoring system 10 incorporating the present invention is shown. The water monitoring system 10 includes an input water sample collection and distribution assembly 12 interconnected by pipes or tubing 24 to one or more remotely located water sampling locations represented by valves 22, and which forms the subject matter of the present invention. System 10 also includes an analyzing sensor assembly 14, receiving filtered and unfiltered sample inputs from assembly 12 via pipes or tubing 30–34, for analyzing and determining the chemistry of aqueous solutions and, in addition, the biological quality of the samples taken from the various remote sampling locations along the process flow path 20 in a water treatment system.

Adjacent the analyzing sensor assembly 14 is located a digital computer 16 which receives analysis data from sensor assembly 14 via cable 38 and provides process and sequencing control signals which control the operation of assemblies 12 and 14 to provide for automated testing of the water samples and which receives status signals from assemblies 12 and 14 as well as data from the sensors of assembly 14. Such sequencing and control signals are sent from computer 16 to assemblies 12 and 14 via cable 26 and receives status information via cable 28. Use of the digital computer 16 allows the water monitoring system 10 to be completely automated, thereby enabling operation of the system with a minimum of personnel. Also included in the water monitoring system 10 is an analog data acquisition assembly 18 designed to receive analog voltage signals representative of the various engineering parameters from computer 16 by signal path 40 and to convert the analog voltage signals into visible engineering unit displays 50 or for storage as by storage means 51 via connections 48. A signal cable 23 provides signal paths from sample collection and distribution assembly 12 to the solenoids of valves 22 at the remote water sampling flow path locations.

Input connections 15, 17 and 19 are provided for deionized water, compressed air, and electrical power, respectively, for use in system 10. Of course, in remote locations or where the water, compressed air or electrical power are not available, suitable sources may be provided which are self-contained within system 10.

Water monitoring system 10 is particularly adaptable for mounting in a typical instrumentation trailer (not shown). When mounted in such a trailer, system 10 is readily transportable to any desired location for use in monitoring the quality of water at that location. For example, such locations include sewage treatment plants, industrial effluent discharges, or other locations where permanent water quality monitoring systems are not feasible or justified. When water monitoring system 10 is positioned adjacent the desired facility, such as a water treatment plant (not shown), a plurality of solenoid-operated valves 22 are positioned in the water treatment flow path 20 to allow the collection of a sample at various points along the process flow path 20. As described above, the sample collections points, including valves 22, may be remote from the sample collection and distribution assembly 12.

Sample collection valves 22 are energized in response to signals received from sample collection and distribution assembly 12 over conductors 23 with the sample collection and distribution assembly 12 being, in turn, controlled by commands from the digital computer 16 over command interface line 26. Additionally, status signals representing the "on-off" condition of valves 22 are transmitted to the digital computer 16 over the status interface line 28. As a valve 22 is energized, a pump contained in the sample collection and distribution assembly 12 is activated, drawing a water sample from the flow path 20, through valve 22 and pipe or tubing 24 into the distribution assembly 12. As will be hereinafter described, the sample is then processed by filters internal to the sample collection and distribution assembly 12 in response to commands from digital computer 16.

Dependent upon the measurement desired, sample collection and distribution assembly 12 can provide the various analyzers in sensor assembly 14 with an unfiltered sample from multi-point valves 22 over lines 30 or 32 or with the filtered sample from one of the multi-point valves 22 over lines 31, 33 or 34. Water samples brought into the analyzing sensor assembly 14 over conduits 30-34 are routed through the various water chemistry analyzers (not shown) and biological detection sub-assemblies within assembly 14 by solenoid valves (not shown) operated by commands from digital computer 16 over command interface line 26.

As will be hereinafter described, sample collection and distribution assembly 12 includes filter units which are capable of removing sediment and other particulate matter from the water as small as 0.45 microns in size. This extremely fine filtration is a requirement for the proper operation of the bio-sensor analyzer sub-assemblies of analyzer assembly 14. Assembly 12 has the capability to automatically clean the internal filters and provide a continuous flow of sample to the analyzing sensors of assembly 14. These features form the subject matter of the present invention as will be further described in further detail below.

As the various analyzers contained within analyzing sensor assembly 14 perform their various functions, the data is collected and transmitted over a sensor-computer data interface to the digital computer 16 for processing. Processed data may then be coupled through a digital to analog convertor (not shown) and then to the analog data acquisition assembly 18 over data interface 40 to provide visual indications of the measurements in an engineering unit display. Additionally, the processed digital data may be output over an interface 42 to provide displays on a cathode ray tube terminal (CRT) 44. As above mentioned, data may also be output over interface 48 to various terminal equipment such as a display device 50 for providing a visual display of the engineering units or to a recording device 51 for storage and later retrieval.

Figure 2:
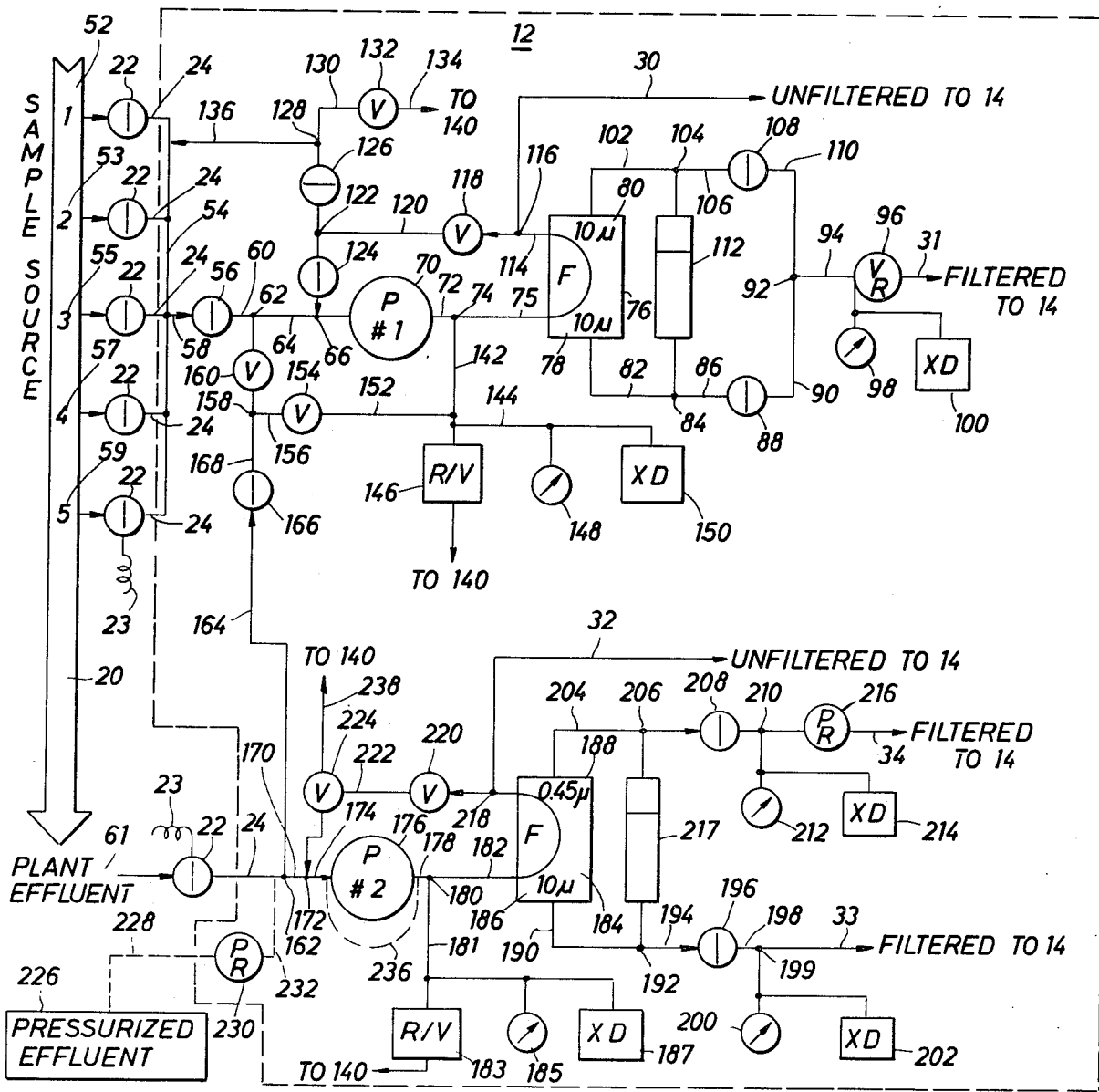
FIG. 2 is a block schematic illustrating the sample collection and distribution sub-assembly in accordance with the methods and apparatus of the present invention.

Referring now to FIG. 2, a selected process flow path 20, such as a sewage treatment process, is shown and includes a plurality of sample stations along the path. For simplicity, five intake stations, 52-59, are positioned along the process flow path 20 with a sixth intake station 61 positioned to receive the sewage treatment plant effluent discharged from process path 20. Each intake station 52-59 is connected to the input of separate electrically-actuated air closure valves 22, the output of each of which is connected to manifold 54. The output of manifold 54 is connected to the input of an electrically actuated air closure valve 56 by tubing 58. The output of valve 56 is connected by tubing 60 to one arm of a "T" connector 62. The remaining arm of "T" connector 62 is connected by tubing 64 to the input of an electrically actuated air closure valve 124 and to the input of a first progressive cavity pump 70. The discharge port of pump 70 is connected to one arm of a "T" connector 74 by tubing 72 with the remaining arm of "T" connector 74 connected by tubing 75 to input port "a" of a dual-filter unit 76. Dual filter unit 76 contains two steel-mesh, ten-micron filters, 78 and 80, with filter 78 positioned to remove particulate matter from the water discharged through port "b" and with filter 80 positioned to remove particulate matter from the water discharged through port "c". Port "b" is connected by tubing 82 to one arm of "T" connector 84 with the remaining arm of "T" connector 84 connected by tubing 86 to the input of a solenoid-operated valve 88. The output port of valve 88 is connected by tubing 90 to one arm of "T" connector 92. The leg of "T" connector 92 is directly connected to the input port of pressure-regulator 96, the output port of which provides a ten-micron, multi-point, filtered sample through line 31 to assembly 14. Additionally, a pressure gauge 98 and a pressure transducer 100, providing pressure status data via status line 28 to computer 16 (see FIG. 1), are interconnected in a conventional manner to the input port of pressure regulator 96.

Discharge port "c" of filter 76 is connected by tubing 102 to one arm of "T" connector 104 with the remaining arm of "T" connector 104 connected by tubing 106 to the input port of a solenoid-operated valve 108. The discharge port valve 108 is connected by tubing 110 to the remaining arm of "T" connector 92. An electrically actuated, double-acting, backwash piston 112 is shown interconnected to the legs of "T" connectors 104 and 84.

Discharge port "d" of filter unit 76 is connected by tubing 114 to one arm of "T" connector 116 with the leg of "T" connector 116 providing a multi-point unfiltered sample through line 30 to assembly 14. The remaining arm of "T" connector 116 is directly connected to the input port of a throttle or flow reduction valve 118 with the discharge port of valve 118 connected by tubing 120 to the leg of "T" connector 122. One arm of "T" connector 122 is connected to the input port of electrically actuated air closure valve 125 with the remaining arm connected to the input port "a" of an "on/off" valve 132 by tubing 130. The discharge port of valve 132 is connected by tubing 134 to system drain 140. The leg of "T" connector 128 is connected by tubing 136 to the manifold 54. The leg of "T" connector 62 is connected to the input of a throttle valve 160, the output of which is connected to one arm of a "T" connector 158. The other arm of "T" connector 158 is connected to the output port of an electrically actuated air closure valve 166. The leg of "T" connector 154 is connected to the input of an "on/off" valve 154 by tubing 156. The output port of valve 154 is connected by lines 152 and 142 around pump 70 to the leg of "T" connector 74. The junction of lines 152 and 142 is connected to the input of a pressure relief valve 146, the output of which is connected to system drain 140. Tubing 144, interconnecting with the junction of lines 152 and 142, is connected to a pressure gauge 148 and pressure transducer 150. The pressure transducer 150 provides a "pressure" signal status indication to analyzer assembly 14 and computer 16, as hereinabove described.

The plant effluent intake station 61 is connected to the input of an electrically actuated air closure valve 22, the output of which is connected by line 24 to one arm of "T" connector 162 with the leg of "T" connector 162 connected to the input port of valve 166 by tubing 164. The remaining arm of "T" connector 162 is connected by tubing 170 to one arm of "T" connector 172 with the remaining arm connected to the input port of a second progressive cavity pump 176. The discharge port of pump 176 is connected by tubing 178 to one arm of "T" connector 180 with the remaining arm of "T" connector connected to port "a" of dual-filter unit 184. The leg of connector 180 is conventionally connected by tubing 181 to a pressure relief valve 183, a pressure gauge 185 and a pressure transducer 187 by line 181. As above-described, pressure transducer 187 provides status indication signals to assembly 14 and computer 16. Pressurized effluent from a suitable fitting 226 may be recovered from process flow path 20 and applied by line 228 to a pressure regulator 230, the output of which is connected to effluent input line 24 by tubing 232.

Second filter unit 184 includes a ten-micron filter 186 associated with discharge port "b" and a 0.45-micron filer 188 associated with discharge port "c". Discharge port "b" is connected by tubing 190 to one arm of "T" connector 192 with the remaining arm connected by tubing 194 to the input of solenoid-operated valve 196. The output of valve 196 is connected to one arm of "T" connector 199 by tubing 198 with the remaining arm of connector 199 providing a ten-micron, effluent, filtered sample through line 33. The leg of "T" connector 199 is conventionally connected to a pressure gauge 200 and a pressure transducer 202 for purposes hereinabove described.

Port "c" of filter 184 is connected by tubing 204 to one arm of "T" connector 206 with the remaining arm connected to the input port of solenoid-operated valve 208. The output of valve 208 is connected to one arm of "T" connector 210 with the remaining arm connected to port "a" of pressure regulator 216. The discharge port of pressure regulator 216 provides a 0.45 micron, effluent, filtered sample through line 34. Additionally, leg of "T" connector 210 is conventionally connected to a pressure gauge 212 and a pressure transducer 214 for purposes hereinabove described. A second, two-port, double-acting electrically-actuated piston 217 is interconnected between the legs of "T" connectors 206 and 192.

Discharge port "d" of filter 184 is connected to one arm of "T" connector 218 with the remaining arm of "T" connector 218 connected to the input of throttle or flow-reduction valve 220. The output valve 220 is connected by tubing 222 to port "a" of electrically actuated discharge valve 224. Output port "b" of valve 224 is connected by tubing 226 to the leg of "T" connector 172. Output port "c" of valve 224 is connected to system drain 140 by means of line 238. In addition, a pump by-pass line 236 is provided that interconnects the input and output ports of pump 176.

Preparatory to operation, it may be required that the system lines be primed by utilizing the pressurized effluent from fitting 226 to force effluent into the various lines and valves. The pressurized effluent passing through pressure regulator 230 from line 228 will enter line 24 and pass into lines 164 and 168 through valve 166. With reduction valve 160 turned to minimum flow and "on-off" valve 154 turned to the "on" position, the pressurized effluent will be discharged from valve 154 to pass into the first filter 76 through lines 152, 142 and 75, exiting via port "d" and through valve 118. In order to prime the manifold 54, valves 124 and 126 are energized, shutting valve 124 and opening valve 126 to allow the effluent to pass through tubing 136 into the manifold 54, thereby priming the system for operation. Additionally, the pressurized effluent flows into output line 30 and, through filter 76 into output line 31. Further, by energizing the by-pass line 236 of pump 176 the pressurized effluent will also be present on output lines 32, 33 and 34.

With the system thus primed, pumps 70 and 176 are energized. Additionally, valve 22 associated with effluent intake station 61 is energized and valve 166 is energized to shut-off the flow between the effluent line 24 and the multi-point input line 60. Further, valves 124 and 126 are deenergized, and valve 56 is energized, as is at least one of the multi-point sample valves 22 associated with the intake stations 52, 53, 55, 57 and 59. A multi-point sample is drawn from the process flow 20 through an energized valve 22 into manifold 54, thence through valve 56 and into pump 70. The valves 22 associated with the intake stations are electrically-actuated, air-operated valves utilizing a rubber liner which is inflated to create a water-tight seal. Thus, the valves 22 are able to pass large particulate matter contained in the water sample without becoming clogged.

Water is discharged from pump 70 into the first filter unit 76. Valves 88 and 108 are also energized to permit the filtered sample to pass therethrough from filter unit 76 into pressure regulator 96 and thence into output tubing 31 as a filtered sample. Periodically, a valve, 88 or 108, is deenergized, and piston 112 is energized to force water back through the filter, thereby backwashing and cleaning it. Further, unfiltered water is discharged from port "d" of filter 76 into the throttle valve 118 which forces a portion of the unfiltered sample into output unfiltered sample line 30. The throttle valve 118 may be adjusted to control the amount of sample from port "d" of filter 76 feeding back into pump 70 to permit precise control of the amount of new sample drawn from manifold 54 by pump 70. Additionally, when necessary, the manifold 54 and associated valves 22 may be backflushed using water from the effluent line 24 by deenergizing valve 166 and energizing valves 124 and 126, allowing pump 70 to draw the effluent from line 24 through valves 166 and 160 and discharge the effluent into input port "a" of filter 76, the output of which is discharged through valve 118 into tubing 120 and into tubing 136 and then into the manifold 54. By opening the multi-point sampling valves 22, one at a time, and closing the valve opened prior to opening a subsequent valve, the multi-point system may be cleared of large obstructions.

As above-described for the multi-point sampling and filtering, effluent may be drawn from line 20 through the associated valve 22 into line 24, with pump 176 discharging the effluent into the second filter 184. Again, a portion of the effluent passes through one filter element 186 which removes particles ten microns or larger for output through valve 196 on line 33. In addition, a portion of the effluent passes through the second different-mesh-size filter element 188 which removes particulate matter 0.45 microns or greater for discharge through valve 208 and pressure regulator 216 to output line 34. As above-described, the filters 186 and 188 may be cleaned by deenergizing the associated valves 196 and 208, and electrically actuating the backflow piston 217 in the proper direction.

In order that the sample collection and distribution system 12 may be automated as above-described, conventional pressure transducers have been utilized to provide pressure status of the system. As may be seen, pressure transducer 150 on the discharge side of the pump 70 and pressure transducer 100 on the discharge side of the filter unit 76 provide a differential pressure indicative of a pressure reduction, which might indicate a clogged filter thereby triggering a filter backwash for filter unit 76 sequence as above described. Similarly, pressure transducer 187 on the discharge side of the pump 176 may be compared with the value obtained from the pressure transducer 214 associated with the 0.45 micron filter or with the pressure transducer 202 associated with the 10 micron filter in the filter unit 184. Again, an increase in the differential pressure will trigger the backwash filter sequence for the filter unit 184.

Although specific embodiments have been described in detail hereinbefore, it is understood that the subject invention is not limited thereto and all variations and modifications thereof are contemplated and are included within the spirit and scope of the invention as defined by the appended claims.

What is claimed is:

1. Apparatus for collecting and distributing an aqueous fluid from a plurality of points along a fluid flow path, comprising:

collecting means for continuously collecting said aqueous fluid from at least one of said plurality of collection points along the fluid flow path;

filter means for receiving said collected aqueous fluid and filtering a portion of said fluid to provide a plurality of filtered sources of the aqueous fluid;

means cooperating with said filter means for providing a source of unfiltered aqueous fluid from a portion of said collected aqueous fluid;

valve means cooperating with said filtered sources of aqueous fluid for periodically halting the flow of one of said filtered sources of the aqueous fluid;

piston means cooperating with said valve means and said filter means for backflushing the filter associated of said first filter means without disrupting the flow of said other sources of filtered aqueous fluid;

first signal generating means for generating first electrical signals representative of the pressure of the unfiltered aqueous fluid after said collecting step but prior to said filtering step;

second signal generating means for generating second electrical signals representative of the pressure of said filtered aqueous fluid in said plurality of filtered sources;

process control means communicating with said apparatus for receiving said first and second electrical signals and for generating and applying thereto electrical command signals for controlling the sequence of operation of each of said means, said collecting means comprising;

inlet means cooperating with said fluid flow path and responsive to command signals from said process control means for admitting said aqeuous fluid from at least one of said plurality of collection points along the fluid flow path; and a pump interconnected to said valve means and responsive to command signals from said process control means for continuously pumping said aqueous fluid from at least one of said plurality of collection points along the fluid flow path.

2. The apparatus as described in claim 1, wherein said filter means comprises a filter unit having an inlet for receiving said fluid from said pump and a plurality of outlets for discharging said pumped fluid, one of said outlets discharging a portion of said fluid passing through said filter unit in an unfiltered condition, the remainder of said outlets having associated therewith filter elements of preselected particulate filter size for discharging the remainder of said fluid as a plurality of filtered sources of the fluid.

3. The apparatus as described in claim 2, wherein said means cooperating with said filter means to provide a source of unfiltered fluid comprises:

a throttle valve receiving said unfiltered fluid discharged from said filter unit and operable to permit only a selected flow of said unfiltered fluid therethrough; and an outlet interconnected between said unfiltered fluid discharge outlet of said filter unit and said throttle valve for permitting a flow of that portion of said unfiltered aqueous fluid discharged from said filter unit that exceeds the capacity of said throttle valve for providing a source of unfiltered aqueous fluid.

4. The apparatus as described in claim 2, wherein said filter unit comprises a dual-filter unit having a pair of filtered discharge outlets, and said valve means comprises a pair of valves each of which is interconnected to one of said filtered discharge outlets of said filter unit for receiving said flow of filtered fluid, said valves operable in response to command signals from said process control means, and wherein said piston means comprises a dual-acting piston interconnected between the inlets of said pair of valve and communicating with said filtered fluid flowing from each of said pair of filter unit discharge outlets, one of said valve closing in response to a command signal from said process control means and said dual-acting piston operable in response to command signals from said process control means for forcing said filtered fluid, the flow of which has been stopped by actuation of said one valve, back through said filter unit discharge outlet for backflushing said filter element associated therewith.

5. The apparatus as described in claim 2, wherein said filter elements are 10-micron filters.

6. Apparatus for collecting and distributing an aqueous fluid from a plurality of points along a fluid treatment flow path including the effluent therefrom, comprising first collecting means for continuously collecting said aqueous fluid from at least one of said plurality of collection points along the fluid treatment flow path;

second collecting means for continuously collecting said aqueous fluid from the effluent from said fluid treatment flow path;

first filter means for receiving said fluid from said first collection means and filtering a portion of said fluid;

sources of the aqueous fluid from said flow path, first means cooperating with said first filter means for providing a source of unfiltered aqueous fluid from a portion of said fluid from said flow path;

second filter means for receiving said fluid from said second collection means and filtering a portion of said effluent aqueous fluid to provide a plurality of filtered sources of the aqueous fluid from said effluent;

second means cooperating with said second filter means providing a source of unfiltered aqueous fluid from a portion of said effluent fluid;

first valve means cooperating with said filtered sources of aqueous fluid from said first filter means for periodically halting the flow of one of said filtered sources of the fluid;

second valve means cooperating with said filtered sources of aqueous fluid from said second filter means for periodically halting the flow of one of said filtered sources of the effluent fluid;

first piston means cooperating with said first valve means and said first filter means for backflushing the associated filter of said first filter means without disrupting the flow of said other sources of filtered aqueous fluid from said first filter means;

second piston means cooperating with said second valve means and said second filter means for backflushing the associated filter of said first filter means without disrupting the flow of said other sources of filtered aqueous fluid from said first filter means;

first signal generating means for generating first electrical signals representative of the pressure of the unfiltered aqueous fluid from said first filter means;

second signal generating means for generating second electrical signals representative of the pressure of said filtered aqueous fluid in said plurality of filtered sources from said first filter means;

third signal generating means for generating third electrical signals representative of the pressure of the unfiltered aqueous effluent fluid from said second filter means;

process control means communicating with said apparatus for receiving said first, second, third and fourth electrical signals and for generating and applying thereto electrical command signals for controlling the sequence of operation of each of said means.

7. The apparatus as described in claim 6, wherein said first collecting means comprises:
   inlet means cooperating with said fluid treatment flow path and responsive to command signals from said process control means for admitting said aqueous fluid from at least one of said plurality of collection points along the fluid treatment flow path; and
   a pump interconnected to said inlet means and responsive to command signals from said process control means for continuously pumping said aqueous fluid from at least one of said plurality of collection points along the fluid treatment flow path.

8. The apparatus as described in claim 7, wherein said first filter means comprises a filter unit having an inlet for receiving said fluid from said pump and a plurality of outlets for discharging said pumped fluid, one of said outlets discharging a portion of said fluid passing through said filter unit in an unfiltered condition, the remainder of said outlets having associated therewith filter elements of preselected particulate filter size for discharging the remainder of said fluid as a plurality of filtered sources of the fluid.

9. The apparatus as described in claim 8, wherein said first means cooperating with said first filter means to provide a source of unfiltered fluid comprises:
   a throttle valve receiving said unfiltered fluid discharged from said filter unit and operable to permit only a selected flow of said unfiltered fluid therethrough; and
   an outlet interconnected between said unfiltered fluid discharge outlet of said filter unit and said throttle valve for permitting a flow of that portion of said unfiltered aqueous fluid discharged from said filter unit that exceeds the capacity of said throttle valve for providing a source of unfiltered aqueous fluid from the fluid treatment flow path.

10. The apparatus as described in claim 8, wherein said filter unit comprises a dual-filter unit having a pair of filtered discharge outlets, and said valve means comprises a pair of valves each of which is interconnected to one of said filtered discharge outlets of said filter unit for receiving said flow of filtered fluid, said valves operable in response to command signals from said process control means, and wherein said piston means comprises a dual-acting piston interconnected between the inlets of said pair of valves and communicating with said filtered fluid flowing from each of said pair of filter unit discharge outlets, one of said valves closing in response to a command signal from said process control means and said dual-acting piston operable in response to command signals from said process control means for forcing said filtered fluid, the flow of which has been stopped by actuation of said one valve, back through said filter unit discharge outlet for backflushing said filter element assocaited therewith.

11. The apparatus as described in claim 8, wherein said filter elements are 10-micron filters.

12. The apparatus as described in claim 7, further including:
   transfer means interconnecting said second collecting means with the input of said pump of said first collecting means; and
   third valve means responsive to command signals from said process control means and cooperating with said transfer means, said pump and said inlet means for permitting the backflushing of said inlet means with aqueous fluid from the effluent collection point when said inlet means becomes clogged with particulate matter present in the aqueous fluid from said fluid treatment flow path.

13. The apparatus as described in claim 6, wherein said second collecting means comprises:
   inlet means cooperating with said fluid flow path effluent and responsive to command signals from said process control means for admitting said aqueous fluid effluent; and
   a pump interconnected to said inlet means and responsive to command signals from said process control means for continuously pumping said aqueous fluid from said collection point of said fluid treatment effluent.

14. The apparatus as described in claim 13, wherein said second filter means comprises a filter unit having an inlet for receiving said fluid from said pump and a plurality of outlets for discharging said pumped fluid, one of said outlets discharging a portion of said fluid passing through said filter unit in an unfiltered condition, the remainder of said outlets having associated therewith filter elements of preselected particulate filter size for discharging the remainder of said fluid as a plurality of filtered sources of the effluent fluid.

15. The apparatus as described in claim 14, wherein said second means cooperating with said second filter means to provide a source of unfiltered effluent fluid comprises:
   a throttle valve receiving said unfiltered fluid discharged from said filter unit and operable to permit only a selected flow of said unfiltered fluid therethrough; and
   an outlet interconnected between said unfiltered fluid discharge outlet of said filter unit and said throttle valve for permitting a flow of that portion of said unfiltered aqueous fluid discharged from said filter unit that exceeds the capacity of said throttle valve for providing a source of unfiltered aqueous fluid from the fluid treatment effluent.

16. The apparatus as described in claim 14, wherein said filter unit comprises a dual-filter unit having a pair of filtered discharge outlets, and said valve means comprises a pair of valves each of which is interconnected to one of said filtered discharge outlets of said filter unit for receiving said flow of filtered fluid, said valves operable in response to command signals from said process control means, and wherein said piston means comprises a dual-acting piston interconnected between inlets of said pair of valves and communicating with said filtered fluid flowing from each of said pair of filter unit discharge outlets, one of said valves closing in response to a command signal from said process control means and said dual-acting piston operable in response to command signals from said process control means for forcing said filtered fluid, the flow of which has been stopped by actuation of said one valve, back through said filter unit discharge outlet for backflushing said filter element associated therewith.

17. The apparatus as described in claim 14, wherein said filter unit is a dual-filter unit having filter elements of different particulate filter size.

18. The apparatus as described in claim 17, wherein one of said filter elements is a 10-micron filter and the other filter element is a 0.45 filter element.

* * * * *